United States Patent [19]

Nowacki

[11] 4,366,105

[45] Dec. 28, 1982

[54] HIGH VOLUME HUMIDIFIER-NEBULIZER

[75] Inventor: Christopher A. Nowacki, Arlington Heights, Ill.

[73] Assignee: Respiratory Care, Inc., Arlington Heights, Ill.

[21] Appl. No.: 289,463

[22] Filed: Aug. 3, 1981

[51] Int. Cl.³ .......................................... A16M 15/00
[52] U.S. Cl. .................... 261/35; 128/203.27;
128/204.13; 261/DIG. 65; 261/104; 261/142
[58] Field of Search ............. 261/DIG. 65, 142, 104,
261/101, 102, 35; 128/203.26, 203.27, 204.13, 204.17

[56] References Cited

U.S. PATENT DOCUMENTS

| | | | |
|---|---|---|---|
| 3,744,771 | 7/1973 | Deaton | 261/DIG. 65 |
| 4,110,419 | 8/1978 | Miller | 261/DIG. 65 |
| 4,172,105 | 10/1979 | Miller et al. | 261/DIG. 65 |
| 4,288,396 | 9/1981 | Ottestad | 261/DIG. 65 |

FOREIGN PATENT DOCUMENTS 1186984  4/1970  United Kingdom ........... 128/204.13

*Primary Examiner*—Tim R. Miles
*Attorney, Agent, or Firm*—Eric P. Schellin

[57] ABSTRACT

A cylindrical cartridge having a housing containing a replinishable water supply is employed as a water supply source for producing an aerosol with an oxygen stream for inhalation therapy to the agency of a nebulizer adapter which couples pressurized oxygen to the cartridge module. The cartridge module is separated in two compartments by means of a metallic disc positioned horizontally in the approximate center thereof and having a tube extending above and below the disc. Water is drawn from the water supply through the tube and into the mixing chamber located above the disc in the cartridge module. The cartridge has a vertical tubular portion with connections to a source of oxygen or air which terminates above the top of the tubing extending through the disc. The aerosol flows out of the cartridge through an outlet nozzle. The cartridge is an elongated housing having a temporary active cylindrical absorption surface means internally above the disc which serves as an evaporating surface.

7 Claims, 2 Drawing Figures

HIGH VOLUME HUMIDIFIER-NEBULIZER

BACKGROUND OF THE INVENTION

The present invention relates to a modification of a high volume humidifier-nebulizer.

U.S. Pat. No. 3,771,221, issued Nov. 13, 1973, relates to inhalation therapy and the medical art of treating with oxygen or a mixture of oxygen and air, having a high moisture content. Several classes of devices including atomizers and humidifiers are adapted for such treatments. With respect to atomizers or nebulizers as they are often called, a heretofore known system for inhalation therapy comprises a container for pure water which has means enabling operation of the container in one of several modes.

U.S. Pat. No. 4,110,419, issued Aug. 29, 1978, relates to a cartridge type humidifier apparatus that includes a separate heater module with a cylindrical opening for replaceably receiving therein disposable cylindrical humidifier cartridge modules. The cartridge modules each have a tubular metal main body adapted for a sliding fit within a complimentary tubular walled heater. The metal tubular body has rigid plastic top and bottom end portions with a separate transverse gas delivery pipe, the gas forming a closed air space over a pool of humidifying liquid. The gas to be humidified is dispersed within a hollow chamber formed between the gas inlet pipe projecting concentrically into the cartridge and the radially spaced wall of the main cartridge body and absorption column. The inlet tube terminates above the water. The subject matter of this patent is incorporated herein by reference. The instant device is a modification of the structure disclosed in this patent to provide a constant water level cartridge humidifier system.

SUMMARY OF THE INVENTION

The invention is hereby concerned with the modification of the device covered in U.S. Pat. No. 4,110,419 that provides breathable inhaled gases that are moisture laden with large quantities of water, for pediatric use. The disposable cylindrical humidifier cartridge modules are modified by separating the cartridge modules into two compartments by means of a disc positioned approximately in the center of the cartridge module. The disc has a tube extending downwardly therefrom for a distance approximately four-fifths of the distance between the disc and the bottom of the cartridge module. The tube extends upwardly from the disc approximately one-half the distance of the downward extension. By use of this modification, water is transferred from the water reservoir to the cartridge but not the reverse. The tube connecting the reservoir with the cartridge contains a ball check valve that prevents backward flow of the water from the cartridge to the reservoir. The water fills the bottom of the cartridge until the tubing is submerged in it and the air around the tubing compresses to a maximum at a given temperature. When the heater is turned on, the trapped air around the center tubing expands and forces the water out of the lower chamber of the column since the check valve prevents the water from flowing back into the reservoir bottle, the water is forced by means of the center tube into the top chamber where it is absorbed by a paper and evaporates into the gas stream. This modification maintains a water level in the cartridge constant independent of the water level in the reservoir bottle.

DETAILED DESCRIPTION OF THE PREFERRED EMBODIMENT

Since the instant application covers the modification of the high volume disposable and semi-disposable cartridge humidifier with self-contained cartridge sterilizing means disclosed in U.S. Pat. No. 4,110,419, only the essential portions of this modified apparatus will be discussed in detail.

Figure 1:
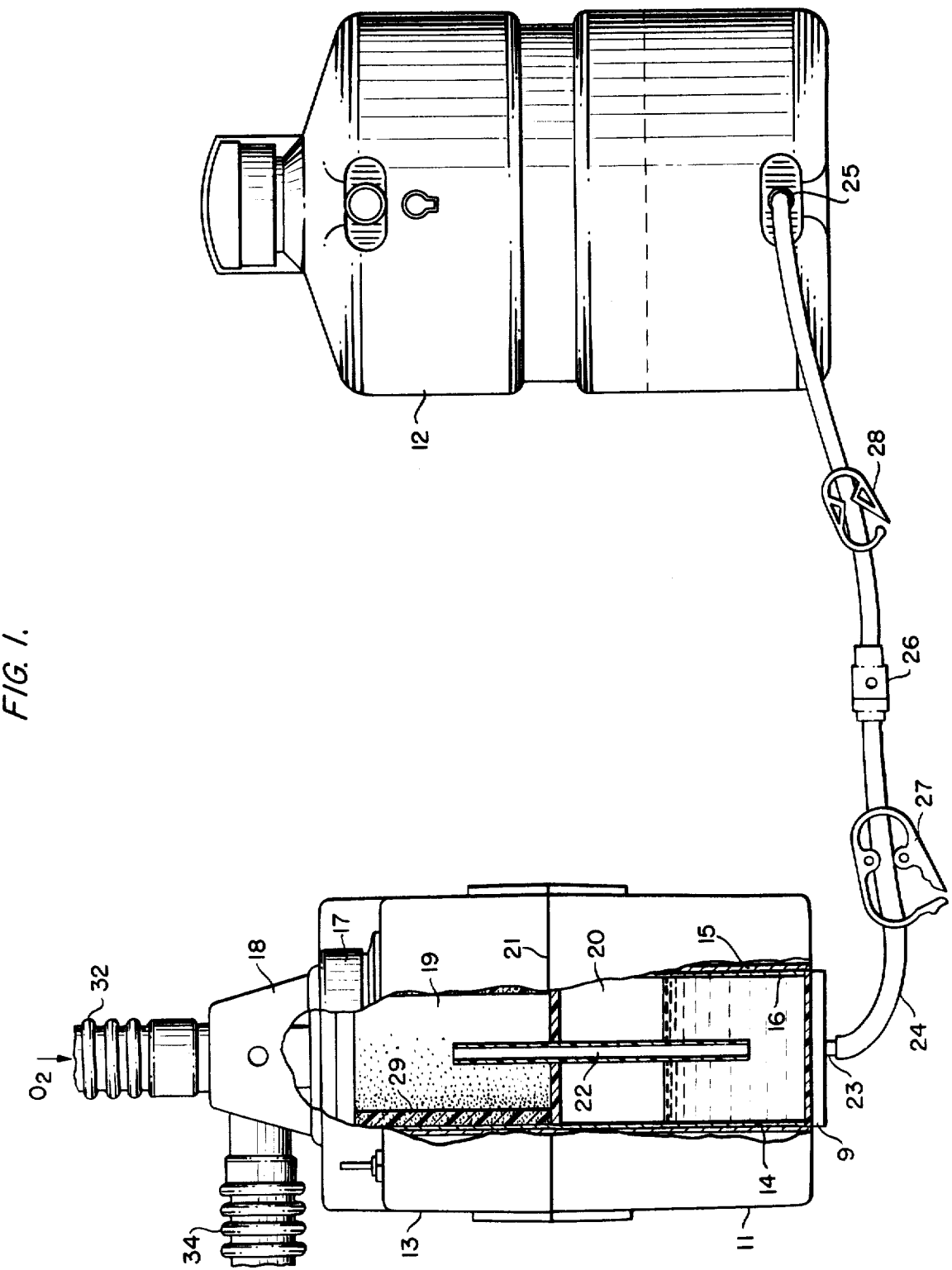
FIG. 1 is a perspective view of the humidifier apparatus showing the detail of the cylindrical humidifier cartridge module in the heater module.

Reference is made to FIG. 1 wherein the modification of the humidifier and neublizer assembly is generally indicated by reference numeral 11. The reservoir bottle is indicated by the reference numeral 12. The heater and cartridge supporting module 13 may comprise any suitable jacket type heater such as an open end metal cylinder sleeve 14 provided with a suitable resistance heating element not shown. Since the heater and the thermostatic controller were not part of this invention and are described in detail in U.S. Pat. No. 4,110,419, they will not be described in detail here. The sleeve 14 may be fabricated from brass tubing or the like having an exemplary diameter of $2\frac{1}{8}$ inches, a 0.051 inch wall thickness and a length range of approximately 5-7 inches, a 100-watt band type heater element in conjunction with the sleeve 14 was found to perform very well and was connected in a conventionally known manner with a single bi-metallic thermostat which may be suitably set to 185° F., to regulate the temperature of the humidified gases passing through the apparatus. The essential feature of the invention resides in the disposable or semi-disposable humidifier cartridge module. A practical form of this disposable or semi-disposable cartridge module 15 may have a cylindrical body composed preferably of a metallic main sleeve member 16 having a preferably nonmetallic top cap 17 and a semi-nonmetallic bottom cap 9 and an exemplary form of the body sleeve corresponding generally to the approximate proportions of FIG. 1. The end caps 17 and 9 to be fabricated of any suitable rigid type plastic material or the like such as polycarbonate material which will not be adversely effected by the heater sleeve 13.

The essential feature of the invention resides in the separation of the cartridge module into two compartments 19 and 20 by a horizontal disc 21 positioned approximately in the center of the cartridge. A tube 22 extends through the disc. The tube 22 extends downwardly from the disc 21 a distance equal to approximately 4/5 of the distance between the disc and the bottom of the cartridge. The tube extends upwardly from the disc approximately $\frac{1}{2}$ the distance of the downward extension. The cartridge module 15 further comprises an absorption column 29 which in one preferred mode is a hollow cylindrical form fabricated of an absorbant blotter-like material for example 3 mm. chromatography paper. Absorption column 29 is positioned in the upper compartment 19 of the cartridge module and is of a size to lay closely against the inside diameter of this portion of the cartridge body. The absorption column functions to absorb the water brought up through the tube 22 to the upper chamber 19 for evaporation therein to moisture-laden gas directed therethrough. The absorption column 26 may extend from the disc 21 to near the top of the cartridge or may be shorter if cartridge of this length is not required for some embodiments.

Figure 2:
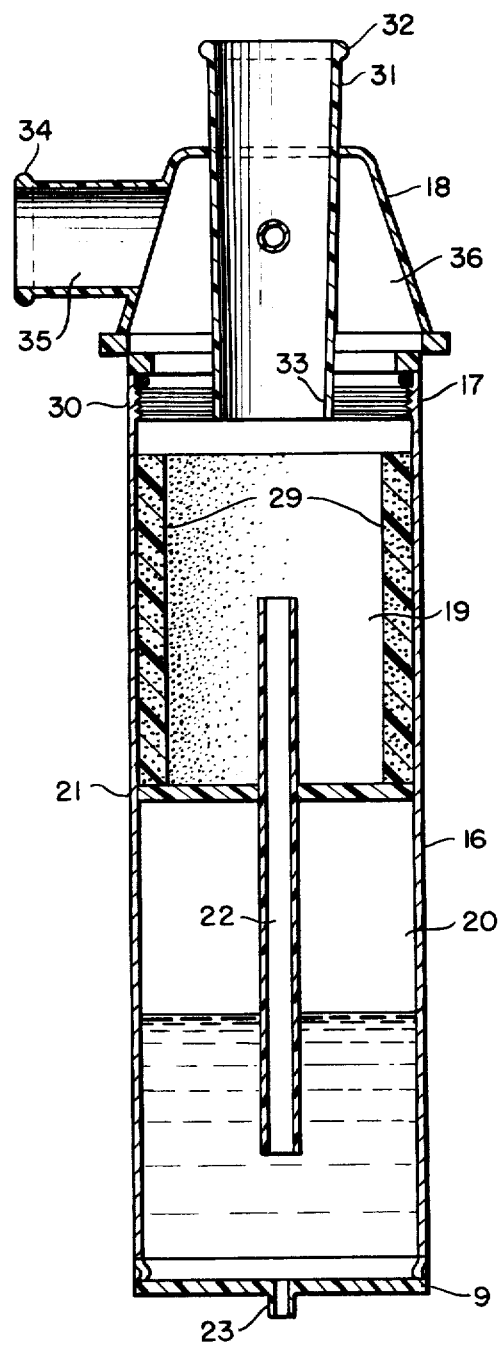
FIG. 2 is a cross sectional view of the modified cylindrical humidifier cartridge.

The upper end cap 17 has its open mouth portion unitarily joined in any suitable manner to the intermediate body sleeve 14. The details of this portion of the device are shown in FIG. 2 and will not be discussed here. The bottom portion of the cartridge 9 has a nipple 23 positioned in the approximate center thereof. A tube 24 is attached to the nipple and extends to the nipple 25 on the reservoir bottle 12. The tube 24 has a check valve 26 such as a ball valve therein and has a manually operable clamps 27 and 28 positioned thereon.

Referring now to FIG. 2 which shows the essential feature of the invention in more detail. The cartridge module 16 is divided into an upper compartment 19 and a lower compartment 20 by the disc 21. The tube 22 extends through the disc 21. The tube extends downwardly for a distance equal to approximately 4/5 of the distance between the disc 21, positioned in the approximate center of the cartridge module and the bottom of the module. The main portion 16 of the module and the disc are made of aluminum or other metallic material for good heat conduction. The bottom portion 9 is made of a suitable plastic material as pointed out above and has a nipple 23 positioned in the approximate center thereof. The upper cap 17 is made of plastic and is attached to the top by thread 29. Cap 17 is uniterally provided with axially centered gas inlet tube 31 having an upwardly projecting outer end 32 adapted to be connected to a source of air or oxygen or oxygen supplemented air and the like. The sleeve 33 extends downwardly to the bottom of the threaded portion 30.

The cap 18 is further provided with a gas delivery port 34 and a connection pipe 35 extending traversly of the axis of the cartridge. The pipe 35 inwardly communicates with the inter radial space 36 defined between the gas inlet tube 32 and the body sleeve 33. In use, a flexible tube is attached to the outlet port 34 and is adapted to deliver the humidified gas to the patient. In use, the water passes from the reservoir bottle 12 on through the tubing 24 and the nipple 23 into the compartment 20 of the cartridge 14. The water fills the compartment 20 of the cartridge until the center tubing 22 is submerged in it and the air around the center tubing compresses to the maximum at a given temperature.

When the cartridge is heated, the air around the center tube 22 expands and forces the water out of the nipple 23 into the tube 22. Since the check valve 26 prevents the water from flowing back into the reservoir bottle, the water is forced via the center tube 22 into the upper chamber 19 where it is absorbed by the absorbant paper 29 and evaporates into the gas stream.

The volume of the water transported into the chamber 19 can be controlled by specifying the internal diameter of the tubing 22 for given operating conditions.

This system avoids the problems in the prior art systems when they are operated at high positive pressures. In these systems the gas washes the water out of the column and back into the bottle. This modification prevents this condition and maintains a constant water level in the cartridge 14 independent of the water level in the reservoir bottle 12.

While one of the preferred embodiments has been illustrated and described in detail, it is apparent that other modifications and changes may be made by those skilled in the art without departing from the inventive spirit thereof. References should be made to the appended claims for the inventive scope covered in this invention.

What is claimed is:

1. A pediatric humidifier cartridge module which is heated by an external heating means, so that said cartridge module supplys both humid and heated breathable gas to a pediatric patient undergoing inhalation therapy, comprising:

a tubular cartridge main body portion having an inner peripheral wall, an upper end portion and a lower end portion, the lower end portion terminates in a transverse wall;

cap means attached to said upper end portion of said main body portion;

liquid inlet means formed in said transverse wall for allowing liquid to pass therethrough;

conduit means connected to said liquid inlet means and adapted to be connected to an external liquid source for supplying liquid to said main body portion;

a check valve positioned in said conduit means;

a disc positioned horizontally in the approximate center of said main body portion and dividing said main body portion into an upper and a lower chamber;

a tube positioned in the approximate center of said disc extending downwardly from said disc and terminating at a point approximately four-fifths of the distance between said disc and the bottom of said main body portion, and extending upwardly from said disc approximately half the distance of the downward extension;

liquid absorption means including an open generally tubular liquid absorption column member with an inner-peripheral face constituting an evaporating surface for humidifying liquid, said column member is disposed generally contiguously and coextensive with said upper chamber of said main body portion and is constructed to be metered by liquid moving into said upper chamber through said tube extending through said disc;

an air space formed by said cap means of said upper end portion together with a portion of said main body portion above the humidifying liquid level in said lower end portion;

a breathable gas inlet feed pipe on said cap means for directing gas to be humidified into said main body portion and terminating in said main body portion; and an outwardly projecting humidified breathable gas outlet delivery pipe on said cap means in fluid communication with said air space, said delivery pipe adapted to be connected to an output delivery tube leading to a patient.

2. The apparatus according to claim 1 wherein the check valve in said conduit connecting said cartridge module with said external liquid source is a ball valve.

3. The apparatus according to claim 2 wherein said ball is of a size sufficient to close the conduit between said cartridge and said external liquid source.

4. The apparatus according to claim 1 wherein the disc separating the cartridge into two chambers is metallic.

5. The apparatus according to claim 4 wherein the disc separating said cartridge into two compartments is about 0.08 to 0.6 centimeters thick.

6. The apparatus according to claim 1 wherein the tube positioned in said disc is fabricated of a rigid plastic material.

7. The apparatus according to claim 6 wherein the tube positioned in said disc has a diameter of about 2 millimeters to 1 centimeter.

* * * * *